United States Patent
Rehrig et al.

(10) Patent No.: US 7,622,853 B2
(45) Date of Patent: Nov. 24, 2009

(54) MICROMACHINED IMAGING TRANSDUCER

(75) Inventors: Paul W. Rehrig, Port Matilda, PA (US); Xiaoning Jiang, State College, PA (US); Wesley S. Hackenberger, State College, PA (US); Jian R. Yuan, Hayward, CA (US); Richard Romley, Tracy, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 494 days.

(21) Appl. No.: 11/202,674

(22) Filed: Aug. 12, 2005

(65) Prior Publication Data

US 2007/0038111 A1    Feb. 15, 2007

(51) Int. Cl.
     *H01L 41/047*      (2006.01)
(52) U.S. Cl. .................. 310/364; 600/459; 29/25.35
(58) Field of Classification Search .......... 600/459, 600/466, 437; 310/311, 334, 357, 367; 367/181; 156/89.12; 29/25.35; 216/83, 102
See application file for complete search history.

(56) References Cited

U.S. PATENT DOCUMENTS

| | | | |
|---|---|---|---|
| 4,683,396 A | | 7/1987 | Takeuchi et al. |
| 4,803,392 A | * | 2/1989 | Kushida et al. ........... 310/311 |
| 5,368,035 A | | 11/1994 | Hamm et al. |
| 5,655,276 A | | 8/1997 | Pattanayak |
| 5,767,612 A | | 6/1998 | Takeuchi et al. |
| 6,019,727 A | | 2/2000 | Koger et al. |
| 6,028,389 A | | 2/2000 | Bernstein |
| 6,183,578 B1 | | 2/2001 | Ritter et al. |
| 6,659,954 B2 | | 12/2003 | Robinson |
| 2001/0042291 A1 | * | 11/2001 | Esashi et al. ............. 29/25.35 |
| 2003/0067249 A1 | * | 4/2003 | Lockwood et al. .......... 310/324 |
| 2003/0114760 A1 | | 6/2003 | Robinson |
| 2004/0085858 A1 | * | 5/2004 | Khuri-Yakub et al. ....... 367/181 |
| 2006/0173348 A1 | * | 8/2006 | Wilser et al. ............. 600/466 |
| 2006/0238067 A1 | * | 10/2006 | Dausch ................... 310/311 |

OTHER PUBLICATIONS

S. Wang, et al, "Deep Reactive Ion Etching of Lead Zirconate Titanate Using Sulfur Hexafluoride Gas", J. Am. Ceram. Soc., 82(5) 1339-1341, 1999.

M. Bale, et al., "Reactive Ion Etching of Piezoelectric $Pb(ZR_xTi_{1-x})O_3$ in a $SF_6$ Plasma", J. Vas. Sci. Technol. A 17(5), pp. 2467-2469, Sep./Oct. 1999.

M. Bale, et al., "Deep Plasma Etching of Piezoelectric PZT with $SF_6$", J. Vas. Sci. Technol. B 19(6), pp. 2020-2025, Nov./Dec. 2001.

(Continued)

*Primary Examiner*—Eric F Winakur
*Assistant Examiner*—Lawrence N Laryea
(74) *Attorney, Agent, or Firm*—Darby & Darby P.C.

(57) ABSTRACT

The present invention generally relates to medical devices, and more particularly to an improved medical imaging device. In one embodiment, an imaging device includes a drive shaft having proximal and distal ends received within the lumen; and an imaging transducer assembly coupled to the distal end of the drive shaft and positioned at the distal portion of the elongate member. The imaging transducer assembly includes one or more imaging transducers formed with a piezoelectric composite plate using photolithography based micromachining.

23 Claims, 6 Drawing Sheets

OTHER PUBLICATIONS

F. Akasheh, et al., "Development of Piezoelectric Micromachined Ultrasonic Transducers", www.sciencedirect.com, Sensors and Actuators A 111, pp. 275-287, 2004.

A.M. Efremov, et al., "Etching Mechanism of Pb(ZR,Ti)$O_3$ Thin films in C$l_2$/Ar Plasma", Plasma Chemistry and Plasma Processing 24(1), pp. 13-28, Mar. 2004.

* cited by examiner

MICROMACHINED IMAGING TRANSDUCER

FIELD OF THE INVENTION

The field of the invention relates to imaging devices, and more particularly to micromachined imaging transducers.

BACKGROUND OF THE INVENTION

Intraluminal, intracavity, intravascular, and intracardiac treatments and diagnosis of medical conditions utilizing minimally invasive procedures are effective tools in many areas of medical practice. These procedures are typically performed using imaging and treatment catheters that are inserted percutaneously into the body and into an accessible vessel of the vascular system at a site remote from the vessel or organ to be diagnosed and/or treated, such as the femoral artery. The catheter is then advanced through the vessels of the vascular system to the region of the body to be treated. The catheter may be equipped with an imaging device, typically an ultrasound imaging device, which is used to locate and diagnose a diseased portion of the body, such as a stenosed region of an artery. For example, U.S. Pat. No. 5,368,035, issued to Hamm et al., the disclosure of which is incorporated herein by reference, describes a catheter having an intravascular ultrasound imaging transducer. These are generally known in the art as Intravascular Ultrasound ("IVUS") devices.

FIG. 1 shows an example of an imaging transducer assembly 1 known in the art. The imaging transducer 1 is typically within the lumen 10 of a guidewire or catheter (partially shown), having an outer tubular wall member 5. To obtain an image of a blood vessel the imaging transducer assembly 1 may be inserted into the vessel. The transducer assembly 1 may then interrogate the cross-sectional-plain of the vessel from the inside by rotating while simultaneously emitting energy pulses, e.g., ultrasound pulses, and receiving echo signals.

On the distal end of the assembly 1 is an imaging element 15, specifically, an imaging transducer 15 that includes a layer of piezoelectric ceramic ("PZT") 80, "sandwiched" between a conductive acoustic lens 70 and a conductive backing material 90, formed from an acoustically absorbent material (e.g., an epoxy substrate having tungsten particles). During operation, the PZT layer 80 is electrically excited by both the backing material 90 and the acoustic lens 70 to cause the emission of energy pulses.

The transducer assembly 1 of FIG. 1 shows a single imaging element 15. Also known in the art is the utilization of an array of imaging elements, e.g., an array of imaging transducers, instead of just one imaging element 15. An array of imaging transducers provides the ability to focus and steer the energy pulses without moving the assembly 1. An example of such an array 100 is shown in FIG. 2, which also illustrates a known process 200 for creating the array 100, commonly referred to as "dice and fill." In the process 200, a plate of poled PZT ceramic 210 is obtained. A saw 220 is then used on the ceramic 210, forming a plurality of kerfs 230 and an array of posts 240, which serve as the PZT layer for the array of transducers 100. The kerfs 230 are then backfilled with polymer materials, such as epoxy 250, to form composite structures. Transducers based on this architecture can exhibit high bandwidth, high sensitivity, good acoustic impedance matching to tissue, and desirable array properties such as low inter-element cross-talk and low side-lobe levels. However, transducers based on this architecture generally do not operate at frequencies much above 20 Megahertz ("MHz"). Accordingly, an improved imaging device would be desirable.

SUMMARY OF THE INVENTION

The present invention generally relates to medical devices, and more particularly to an improved medical imaging device. In one embodiment, an imaging device includes a drive shaft having proximal and distal ends received within the lumen; and an imaging transducer assembly coupled to the distal end of the drive shaft and positioned at the distal portion of the elongate member. The imaging transducer assembly includes one or more imaging transducers formed with a piezoelectric composite plate using photolithography based micromachining.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the present inventions are obtained, a more particular description of the invention briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

DETAILED DESCRIPTION OF THE PREFERRED EMBODIMENTS

Figure 1:
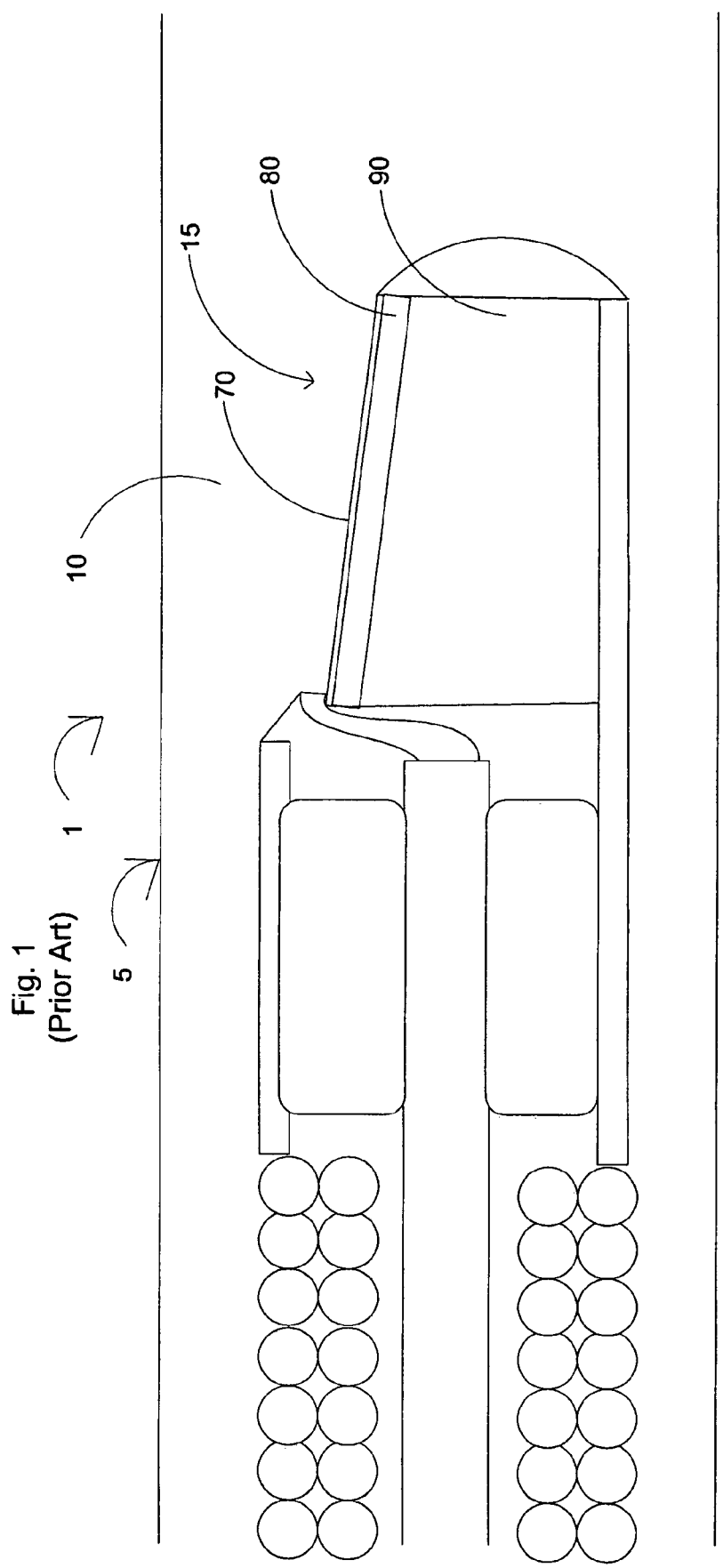
FIG. 1 is a cross-sectional side view of an imaging transducer assembly known in the art.
Figure 2:
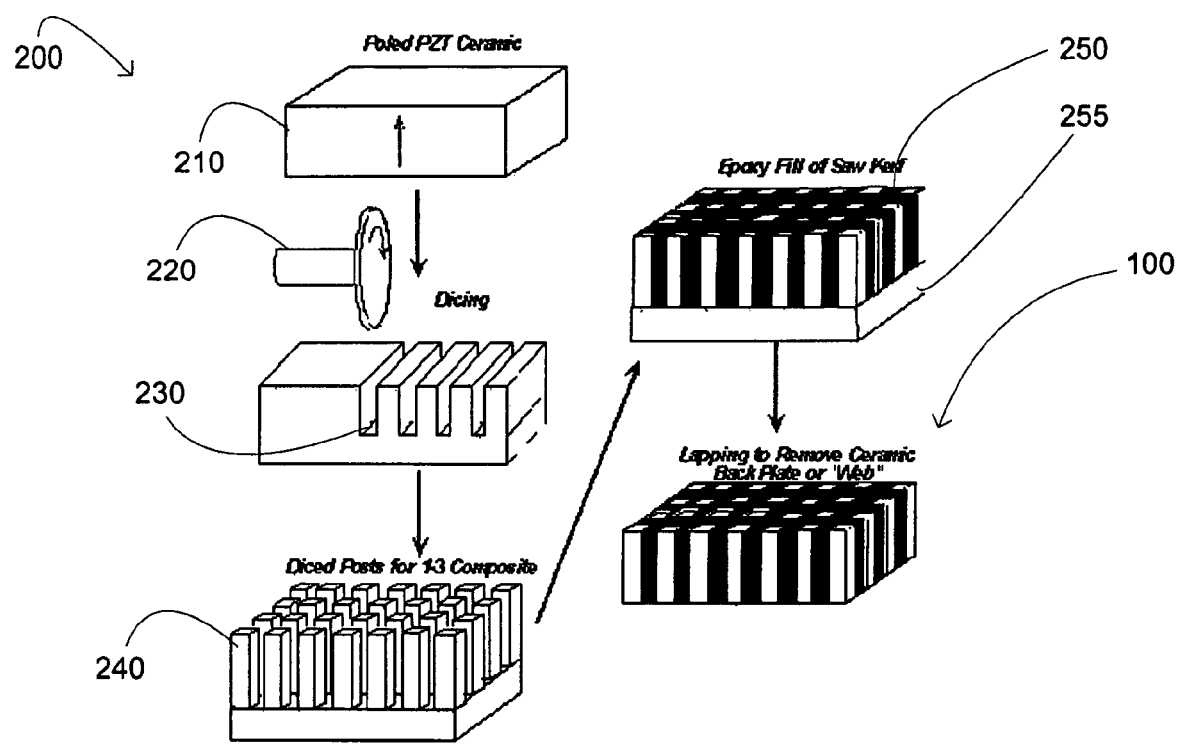
FIG. 2 is an illustration of a technique for manufacturing an array of transducers known in the art.
Figure 3:
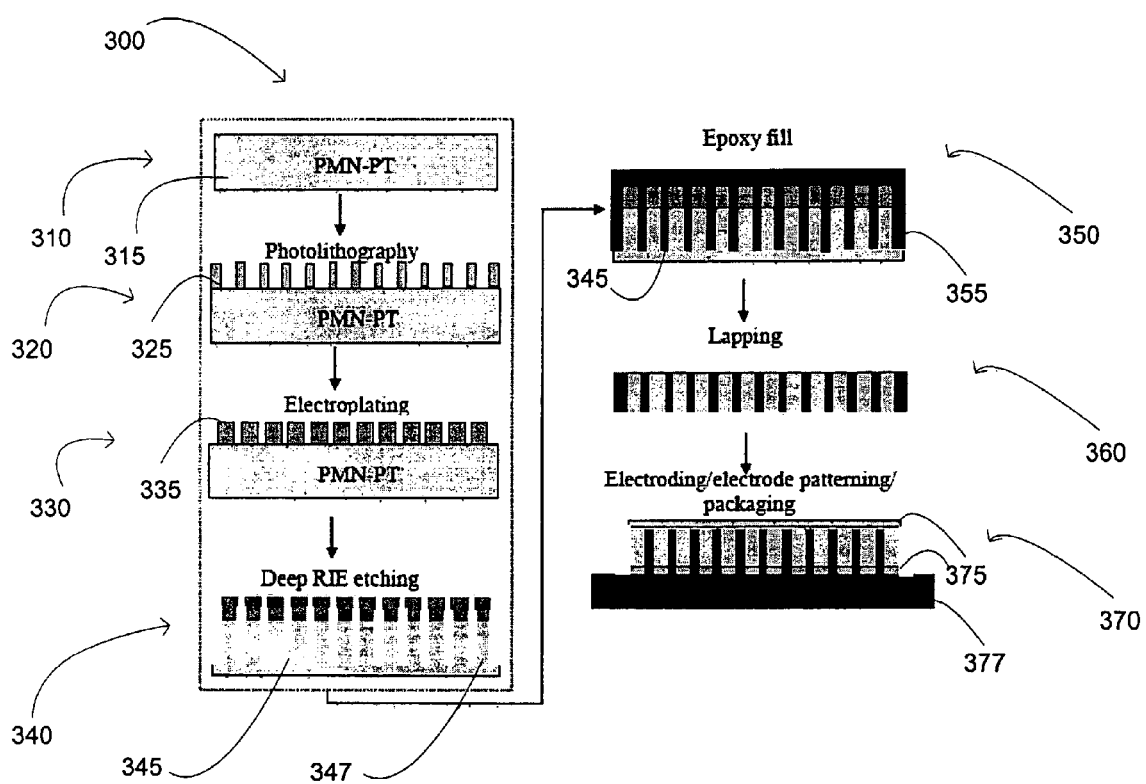
FIG. 3 is an illustration of a photolithography based micromachining process in accordance with a preferred embodiment of the present invention.

As mentioned above, an imaging transducer that operates at high frequencies, e.g., frequencies higher than 20 MHz, would be desirable. Such imaging transducers can provide images with higher resolution, which is desirable in applications involving dermatology, ophthalmology, laparoscopy, intracardiac and intravascular ultrasound. One approach to develop such imaging transducers is to utilize a photolithography based micromachining process. An example of such a process 300 is illustrated in FIG. 3.

In the first step 310, a plate or block of piezoelectric crystal material 315, such as lead magnesium niobate lead titanate ("PMN-PT") or lead zinc niobate-lead titanate ("PZN-PT") is obtained. The plate 315 is preferably lapped on both sides and polished on one of the sides. The lapped and unpolished side can then be bonded to a glass carrier (not shown), which is bonded to a silicon, Si, wafer (not shown). The dimensions of the plate 315 are in the range of ten (10) millimeters ("mm")× ten (10) mm×0.5 mm to fifteen (15) mm×fifteen (15) mm×0.5 mm; however, the dimensions could be of any size. The material of the plate 315 can be a ceramic or a single crystal. Preferably, the material of the plate 315 is a single crystal PMN-PT with electroded faces oriented along the <001> or <011> crystallographic directions. As one of ordinary skill in the art would appreciate, a single crystal structure can desirably have a high piezoelectric coefficient (e.g., $d_{33}$>1500 pC/N, $k_{33}$>0.8, $k_{33}'$>0.7). The plate 315 preferably has a dielectric constant in the range of approximately 4000 to >7700 and a dielectric loss of less than 0.01.

In the next step 320, a mask of photoresist 325 is applied to the plate of piezoelectric material 315. The mask 325 defines the desired shape and/or pattern of imaging element(s) within the piezoelectric composite material 315. In the next step 330, electroplating is applied to the plate 315 using nickel, Ni. A hard pattern of Ni 335 is formed on the plate 315 in accordance with the mask of photoresist 325. The pattern of Ni 335 can have a thickness of approximately 1 to 20 microns ("μm"). Other metals, such as platinum, Pt, may be used instead of, or in addition to, nickel. The use of hard and/or high molecular weight materials, such as Ni and Pt, is desirable for selectivity, to protect the covered underlying area of the plate 315 from being etched. The mask of photoresist 325 is removed after the Ni is applied.

In the next step 340, an etching process, such as reactive ion etching ("RIE"), is applied. Other etching processes can be used, such as wet-etching. In one preferred embodiment, chlorine, $Cl_2$ based RIE etching is used, which has an etching rate of approximately from less than 3 microns/hour to 12 microns/hour and can cause a substantially vertical etching profile (e.g., >80°). In the alternative, or in addition, to $Cl_2$, sulfur hexafluoride, $SF_6$, based etching can be used, which has similar etching properties to that of $Cl_2$. The nickel, Ni, pattern 335 protects the underlying portions of the plate 315 covered by the pattern 335 from the etching process, and thus, one or more deep posts 347 are formed in the plate 315 with one or more kerfs 345 surrounding the one or more posts 347 etched in the uncovered portions of the plate 315. The one or more kerfs 345 can have a width in the range of approximately from less than one (<1) to twelve (12) μm, and the width of the one or more posts 347 can have a width in the range of approximately from less than three (<3) to thirty-six (36) μm and have a height in the range of approximately from less than five (<5) to more than seventy (>70) μm. In one embodiment, it is preferable to have an aspect ratio (post height/post width) of at least two (2) to one (1) to dampen the effect of lateral modes. For the dimensions of the plate 315 described above, the etching process can last approximately six (6) to eight or eighteen (8 or 8) hours. After the etching step 340, the plate 315 is then rinsed with a solvent for cleaning.

In the next step 350, the kerfs 345 are filled with an epoxy 355 such as Epo-Tek-301. A vacuum (not shown) may be utilized to remove air bubbles and prevent any void within the kerfs 345. In the next step 360, the top portion of the plate 315 and epoxy 355 are lapped to a thickness of approximately forty (40) μm. An electrode pattern 375 is then applied to the plate 315 in the next step 370 to form the imaging transducer pattern. The electrode pattern 375 is preferably comprised of gold, Au, and chromium, Cr. Moreover, as one of ordinary skill in the art would appreciate, electronic circuitry, such as imaging processing circuitry, (not shown) can be bonded to the electrodes 375. Further, the electrode pattern 375 formed on the plate 315 can define any pattern of imaging transducers, including an array, e.g., an imaging transducer at each post 347, or a single imaging transducer. An epoxy layer 377 may be applied to the back of the plate 315.

Imaging transducers having an operating frequency at above 20 MHz, e.g., 30 to >80 MHz, can be developed using photolithography based micromachining, such as the process 300 described above. The higher frequency of operation increases the resolution and image depth of an imaging transducer. Furthermore, the bandwidth of the imaging transducer, particularly when single crystal PMN-PT is employed as the piezoelectric, can be close to 100%, compared to only 70 to 80% for <20 MHz transducers made with PZT ceramic. The greater bandwidth improves the transducer's axial resolution, which increases the imaging depth. This is desirable for high frequency transducers, which have very limited imaging depth due the strong attenuation of high frequency ultrasound in tissue. When single crystal is used, these advantages can be achieved with sensitivities equivalent to or better than ceramic transducers. These high frequency transducers can be applied to a number of medical procedures including the imaging of the anterior region of an eye for monitoring surgical procedures such as cataract treatment by lens replacement and laser in situ keratomileusis (LASIK) and tumor detection (preferably up to sixty (60) MHz for fifty (50) μm resolution); skin imaging for care of burn victims and melanoma detection (preferably twenty five (25) MHz for subcutaneous, fifty (50) MHz for dermis and one hundred plus (100+) MHz for epidermis); intra-articular imaging for detection of pre-arthritis conditions (preferably twenty five (25) to fifty (50) MHz); in-vivo mouse embryo imaging for medical research (preferably fifty (50) to sixty (60) MHz); Doppler ultrasound for determination of blood flow in vessels<one hundred (100) μm in diameter (preferably twenty (20) to sixty (60) MHz); intracardiac and intravascular imaging (preferably ten (10) to fifty (50) MHz); and ultrasound guidance for the biopsy of tissue.

Figure 4A:
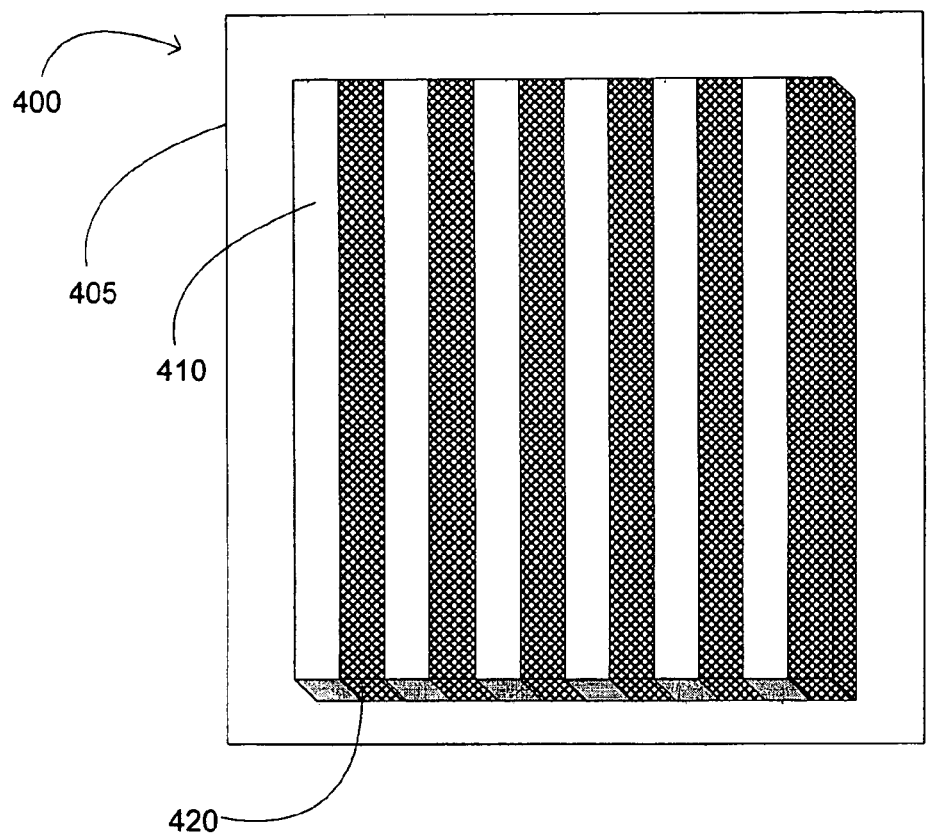
FIG. 4a is an imaging transducer having a 2-2 configuration in accordance with a preferred embodiment of the present invention.
Figure 4B:
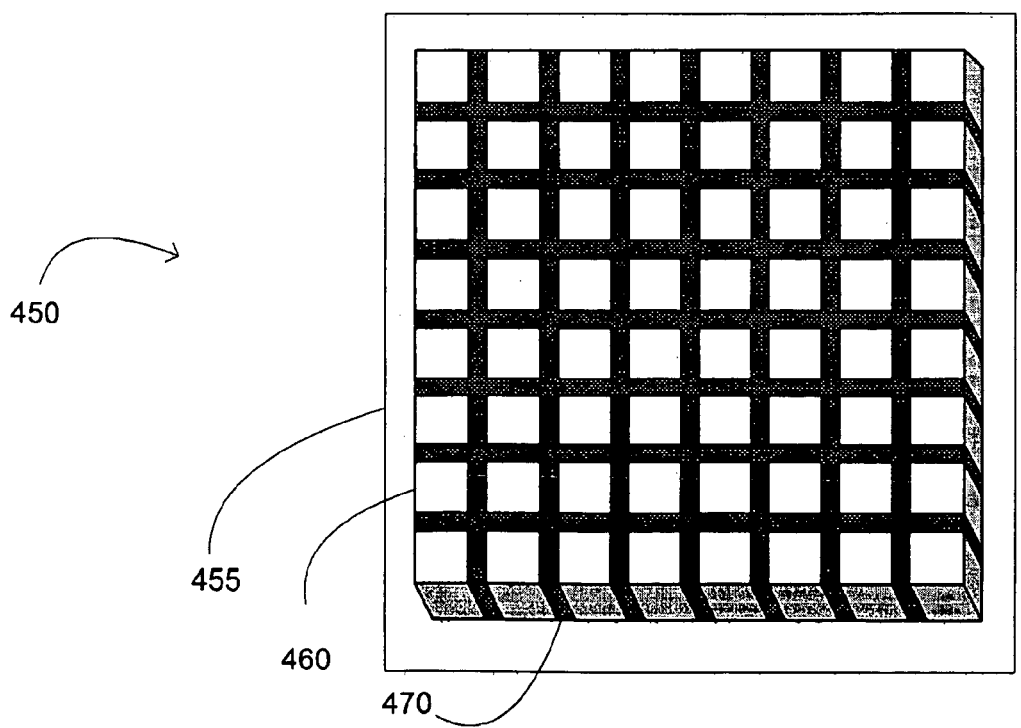
FIG. 4b is an imaging transducer having a 1-3 configuration in accordance with a preferred embodiment of the present invention.

In preferred embodiments, at least two types of imaging transducer configurations can be developed using a photolithography based micromachining process, such as the process 300 described above, the 2-2 configuration and the 1-3 configuration, which are configurations known in the art. Turning to FIG. 4a, an example array 400 of piezoelectric posts 410 are shown on a wafer 405 positioned in a 2-2 configuration. Polymeric material 420 is filled in between the posts 410. The "2-2" describes the number of directions in which each section of the piezoelectric material 410 and polymeric material 420 mainly extend. The description method preferably uses an M-N labeling convention, where M is the number of directions in which the piezoelectric material 410 mainly extends and N is the number of directions in which the polymeric material 420 mainly extends. Turning to FIG. 4b, an example array 450 of piezoelectric posts 460 are shown on a wafer 455 positioned in a 1-3 configuration. The kerfs 470 in between the posts 460 are filled with a polymeric material.

Using a photolithography based micromachining process, such as the process 300 described above, on a plate of piezoelectric material enables any pattern of imaging elements to be formed, including one dimensional and two dimensional arrays of imaging elements, which can be utilized in two dimensional and three dimensional ultrasound imaging applications, respectively.

Figure 5A:
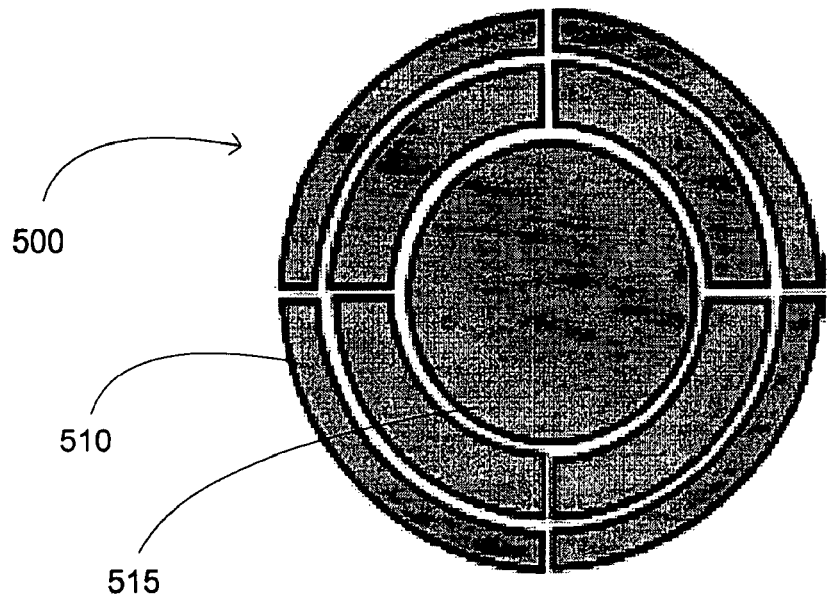
FIG. 5a is an annular transducer array in accordance with a preferred embodiment of the present invention.
Figure 5B:
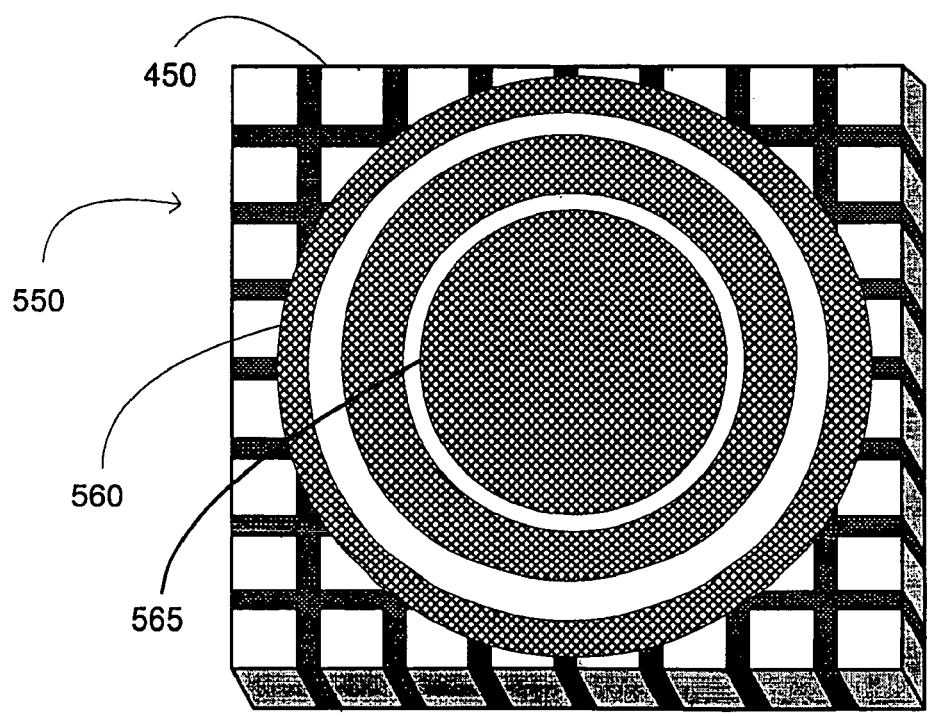
FIG. 5b is another annular transducer array in accordance with a preferred embodiment of the present invention.

In addition, various shapes of arrays may be formed. Turning to FIG. 5a, an annular array 500 of imaging transducers is shown. The array includes segmented elements 510 and a central element 515. Turning to FIG. 5b, an alternative annular array 550 of imaging transducers is shown. The array 550 includes a central element 565 and annular aperture elements 560 concentrically positioned around the central element 565. These annular array configurations may be forward-facing in an imaging catheter or guidewire and are particularly suited for blood vessels. The annular arrays are preferably formed by defining annular arrays of electrodes over a 1-3 composite structure 450, such as that shown in FIG. 4b.

Figure 6:
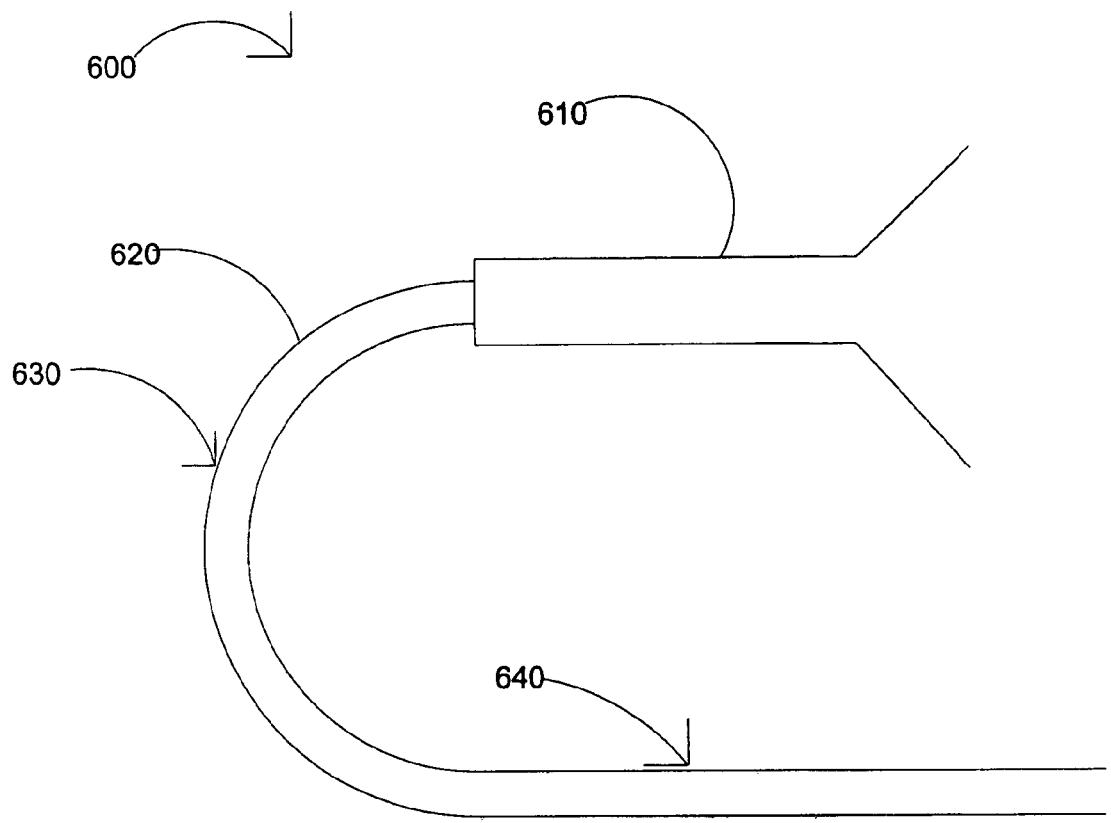
FIG. 6 is a cross-sectional view of an imaging wire in accordance with a preferred embodiment of the present invention.

Turning to FIG. 6, the imaging transducers described above may be used in a catheter and can also be placed in a distal portion 640 of a guidewire 600. The guidewire 600 may comprise a guidewire body 620 in the form of a flexible, elongate tubular member, having an outer wall 630. The guidewire body 620 may be formed of any material known in the art including nitinol hypertube, metal alloys, composite materials, plastics, braided polyimide, polyethylene, peek braids, stainless steel, or other superelastic materials.

Figure 7:
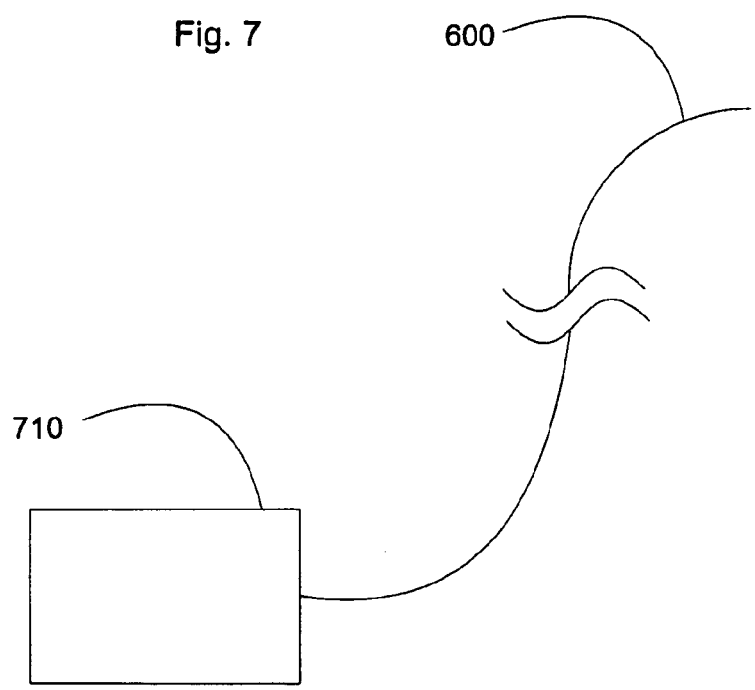
FIG. 7 is a diagram of a medical imaging system in accordance with a preferred embodiment of the present invention.

Turning to FIG. 7, a proximal portion of the guidewire 600, such as that shown in FIG. 6, may be adapted to connect to circuitry 710 that processes imaging signals from the imaging transducers described above, such circuits being well known.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention can be performed using different or additional process actions, or a different combination or ordering of process actions. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. An imaging device configured to be located in an imaging catheter, said imaging device comprising:
a drive shaft having proximal and distal ends; and
an imaging transducer assembly coupled to the drive shaft, wherein the imaging transducer assembly includes one or more imaging transducers, wherein the one or more imaging transducers are formed from a photolithography based micromachined piezoelectric composite plate, the piezoelectric composite plate including a single crystal piezoelectric, wherein each imaging transducer includes a plurality of posts and each of the plurality of posts has an aspect ratio of post height to post width of at least 2 to 1.

2. The imaging device of claim 1, wherein at least one of one or more imaging transducers is in a 2-2 configuration or a 1-3 configuration.

3. The imaging device of claim 1, wherein the one or more imaging transducers is one of a one dimensional array of imaging transducers or a two dimensional array of imaging transducers.

4. The imaging device of claim 1, wherein the one or more imaging transducers are forward facing.

5. The imaging device of claim 1, wherein the one or more imaging transducers form an annular array.

6. The imaging device of claim 1, wherein the one or more imaging transducers operate at a frequency of at least 20 MHz.

7. The imaging device of claim 1, wherein the one or more imaging transducers operate at a frequency of at least 100 MHz.

8. The imaging device of claim 1, wherein the one or more imaging transducers have an operating bandwidth of at least 80%.

9. The imaging device of claim 1, wherein the one or more imaging transducers includes a plurality of kerfs, wherein each of the plurality of posts has a width in the range of approximately 3 to 36 μm and each of the plurality of kerfs has a width in the range of approximately 1 to 15 μm.

10. The imaging device of claim 1, wherein a plurality of the imaging transducers are in a 1-3 configuration, and the imaging device further comprises an annular array of electrodes over the imaging transducers.

11. The imaging device of claim 1, wherein the photolithography based micromachined piezoelectric composite plate is formed, at least in part, by:
forming a hard metal mask over portions of a composite plate where a plurality of posts are to be formed; and
etching portions of the plate exposed by the hard mask to form a plurality of kerfs between the posts, wherein the kerfs do not extend through the plate after the etching; and
filling the plurality of kerfs surrounding the plurality of posts with a polymeric material.

12. The imaging device of claim 1, wherein each of the plurality of posts has a vertical etching profile of at least 80°.

13. A method for fabricating one or more imaging transducers, comprising the steps of:
using photolithography based micromachining to form a plurality of posts on a piezoelectric material plate, wherein the step of forming a plurality of posts on a piezoelectric material plate using photolithography based micromachining comprises
forming a hard metal mask over portions of the plate where the plurality of posts are to be formed; and
etching portions of the plate exposed by the hard mask to form a plurality of kerfs between the posts, wherein the kerfs do not extend through the plate after the etching and wherein the posts have an aspect ratio of at least 2 to 1 and a vertical etching profile of at least 80°; and
filling the plurality of kerfs surrounding the plurality of posts with a polymeric material;
wherein the one or more imaging transducers are ultrasound transducers.

14. The method of claim 13, wherein the one or more imaging transducers operate at a frequency of at least 20 MHz.

15. The method of claim 13, wherein at least one of the one or more imaging transducers is in a 2-2 configuration or a 1-3 configuration.

16. The method of claim 13, wherein the one or more imaging transducers is one of a one dimensional array of imaging transducers and a two dimensional array of imaging transducers.

17. The method of claim 13, wherein the one or more imaging transducers form an annular array.

18. The method of claim 13, wherein the one or more imaging transducers includes a plurality of posts and kerfs, wherein each of the plurality of posts has a width in the range of approximately 3 to 36 μm and each of the plurality of kerfs has a width in the range of approximately 1 to 15 μm.

19. The method of claim 13, wherein the one or more imaging transducers have an operating bandwidth of at least 80%.

20. The method of claim 13, wherein after the etching of the portions of the plate, an upper portion of each post is separated from an upper portion of adjacent posts only by the plurality of kerfs.

21. The method of claim 13, wherein etching portions of the plate comprises etching portions of the plate leaving a bottom region unetched and connecting the plurality of posts; the method further comprising removing the bottom region after filling the plurality of kerfs with the polymeric material.

22. A method for fabricating one or more imaging transducers, comprising the steps of:
using photolithography based micromachining to form a plurality of posts on a piezoelectric material plate, wherein the step of forming a plurality of posts on a piezoelectric material plate using photolithography based micromachining comprises
forming a hard metal mask over portions of the plate where the plurality of posts are to be formed; and
selectively etching portions of the plate exposed by the hard mask to form a plurality of kerfs surrounding the post, wherein, after the etching of the portions of the plate, an upper portion of each post is separated from an upper portion of adjacent posts only by the plurality of kerfs; and
filling the plurality of kerfs surrounding the plurality of posts with a polymeric material;
wherein the one or more imaging transducers includes a plurality of posts and kerfs, wherein each of the plurality of posts has a width in the range of approximately 3 to 36 μm, an aspect ratio of at least 2 to 1, and a vertical etching profile of at least 80°, and each of the plurality of kerfs has a width in the range of approximately 1 to 15 μm.

23. The method of claim 22, wherein etching portions of the plate comprises etching portions of the plate leaving a bottom region unetched and connecting the plurality of posts; the method further comprising removing the bottom region after filling the plurality of kerfs with the polymeric material.

* * * * *

UNITED STATES PATENT AND TRADEMARK OFFICE
CERTIFICATE OF CORRECTION

PATENT NO. : 7,622,853 B2  Page 1 of 1
APPLICATION NO. : 11/202674
DATED : November 24, 2009
INVENTOR(S) : Rehrig et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 935 days.

Signed and Sealed this

Twenty-sixth Day of October, 2010

David J. Kappos
*Director of the United States Patent and Trademark Office*